(12) United States Patent
Russell

(10) Patent No.: US 10,743,747 B2
(45) Date of Patent: Aug. 18, 2020

(54) ARTICULATION JOINT MANUFACTURING PROCESS AND WORKPIECE THEREFOR

(71) Applicant: Okay Industries, Inc., New Britain, CT (US)

(72) Inventor: Shawn H. Russell, Bristol, CT (US)

(73) Assignee: Okay Industries, Inc., New Britain, CT (US)

( * ) Notice: Subject to any disclaimer, the term of this patent is extended or adjusted under 35 U.S.C. 154(b) by 113 days.

(21) Appl. No.: 16/169,196

(22) Filed: Oct. 24, 2018

(65) Prior Publication Data

US 2019/0142241 A1 May 16, 2019

Related U.S. Application Data

(60) Provisional application No. 62/586,344, filed on Nov. 15, 2017.

(51) Int. Cl.

| A61B 1/00 | (2006.01) |
|---|---|
| A61M 25/01 | (2006.01) |
| B23P 21/00 | (2006.01) |
| B23P 19/04 | (2006.01) |
| B23K 26/00 | (2014.01) |
| B23D 21/00 | (2006.01) |
| B23D 31/00 | (2006.01) |

(Continued)

(52) U.S. Cl.
CPC ............ *A61B 1/0011* (2013.01); *A61B 1/008* (2013.01); *A61B 1/0055* (2013.01); *A61B 1/00119* (2013.01); *A61B 1/00128* (2013.01); *B23D 21/00* (2013.01); *B23D 23/04* (2013.01); *B23D 31/002* (2013.01); *B23K 26/0093* (2013.01); *B23P 15/00* (2013.01); *B23P 19/048* (2013.01); *B23P 21/00* (2013.01); *A61M 25/0138* (2013.01)

(58) Field of Classification Search
CPC ..... A61B 1/008; A61B 1/0011; A61B 1/0015; A61B 1/00119; A61B 1/00128; A61M 25/0138; B23D 23/04; B23D 31/002; B23D 21/00; B23P 15/00; B23P 19/048; B23P 21/00; B23K 26/0093
See application file for complete search history.

(56) References Cited

U.S. PATENT DOCUMENTS

| 7,578,786 B2 * | 8/2009 | Boulais ............... A61B 1/00059 600/141 |
|---|---|---|
| 7,591,783 B2 * | 9/2009 | Boulais ............... A61B 1/00059 600/139 |

(Continued)

*Primary Examiner* — Bayan Salone
(74) *Attorney, Agent, or Firm* — Alix, Yale & Ristas, LLP

(57) ABSTRACT

An articulation joint manufacturing process comprises cutting an elongated tube to form a multiplicity of links wherein adjacent links are connected by a bridge. The method comprises forming a fracturable portion on each bridge and connecting a multiplicity of springs to adjacentts links to form a workpiece. The method further comprises applying a torsional force to the workpiece about its longitudinal axis to fracture each bridge to form an articulation joint comprising a series of links wherein adjacent links are connected by at least one spring. Certain steps are formed by a laser. In one method, the springs are positioned on a mandrel and the springs are welded to the workpiece. The fracturable portion on the bridges may be produced by forming an indentation which may be a score, a perforation, an elongated indentation or an oval shaped indentation.

20 Claims, 11 Drawing Sheets

(51) Int. Cl.
  *B23P 15/00* (2006.01)
  *A61B 1/005* (2006.01)
  *B23D 23/04* (2006.01)
  *A61B 1/008* (2006.01)

(56) References Cited

U.S. PATENT DOCUMENTS

| | | | | |
|---|---|---|---|---|
| 8,118,732 | B2* | 2/2012 | Banik | A61B 1/00059 600/117 |
| 8,425,408 | B2* | 4/2013 | Boulais | A61B 1/00059 600/139 |
| 8,535,219 | B2* | 9/2013 | Smith | A61B 1/00059 600/127 |
| 2005/0131279 | A1* | 6/2005 | Boulais | A61B 1/00059 600/141 |
| 2005/0245789 | A1* | 11/2005 | Smith | A61B 1/00059 600/159 |
| 2008/0269561 | A1* | 10/2008 | Banik | A61B 1/0051 600/141 |
| 2010/0048999 | A1* | 2/2010 | Boulais | A61B 1/00059 600/141 |
| 2010/0076266 | A1* | 3/2010 | Boulais | A61B 1/00059 600/142 |
| 2014/0073852 | A1* | 3/2014 | Banik | A61B 1/00059 600/103 |
| 2014/0088358 | A1* | 3/2014 | Banik | A61B 1/0052 600/109 |
| 2015/0216396 | A1* | 8/2015 | Banik | A61B 1/00059 600/103 |

* cited by examiner

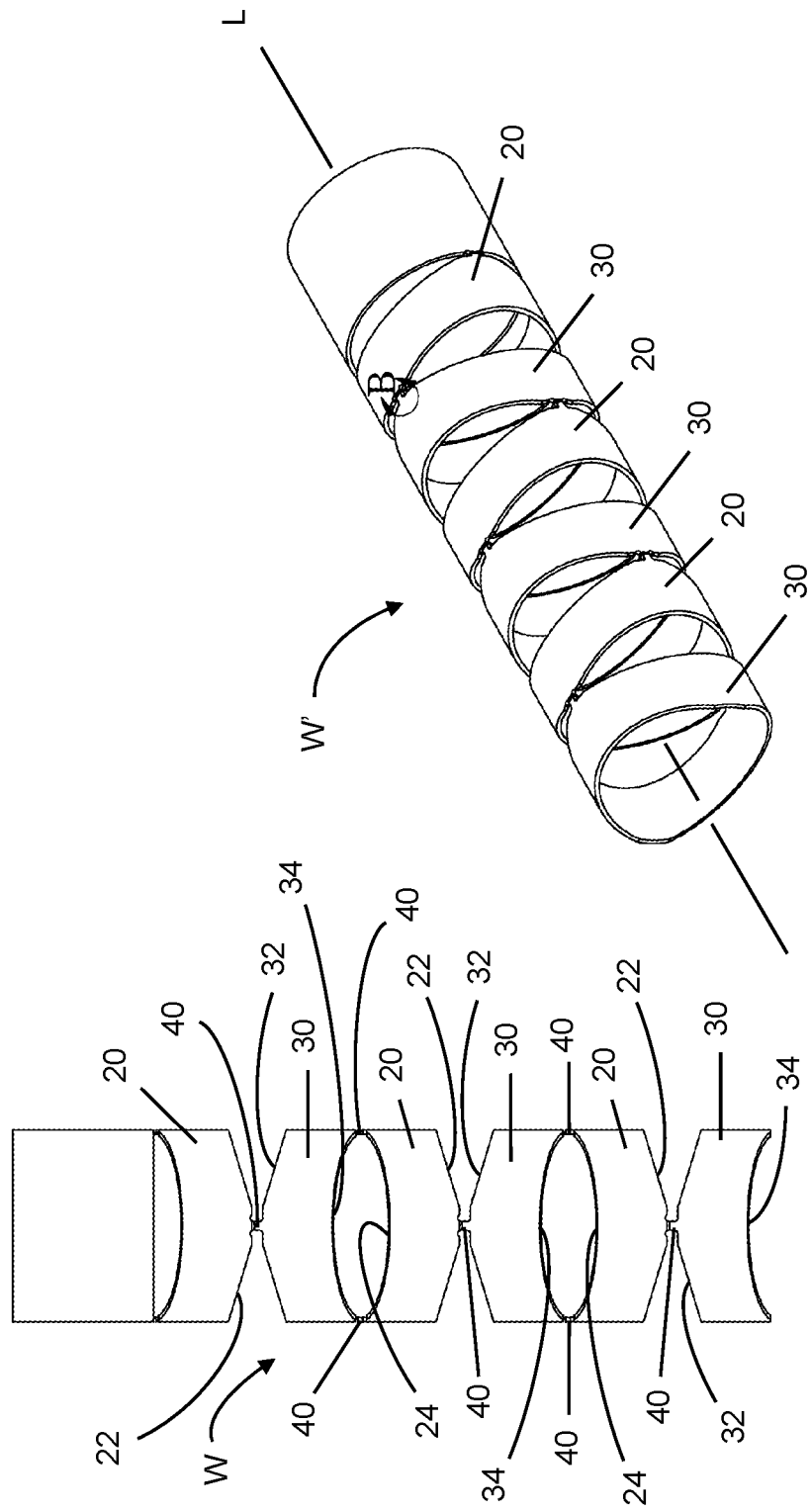

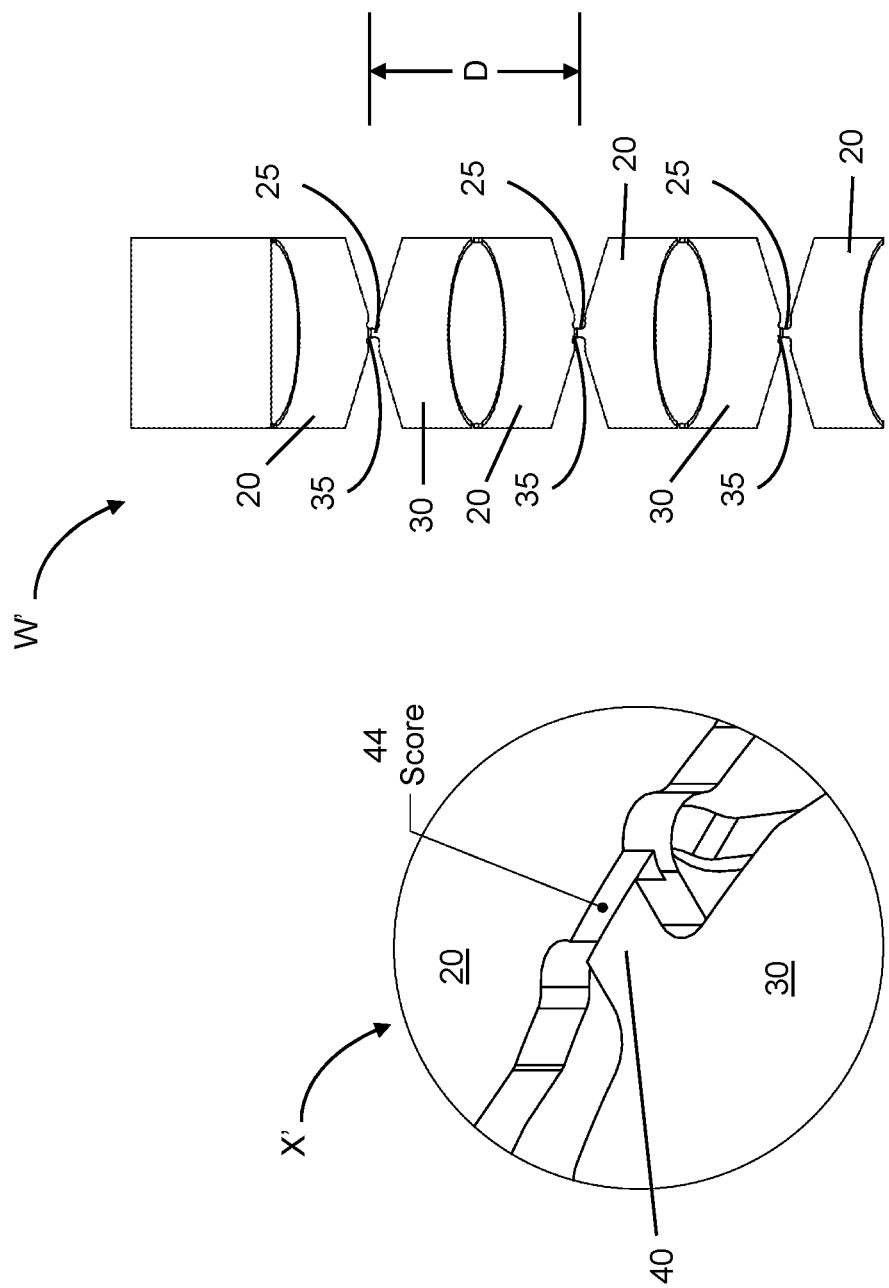

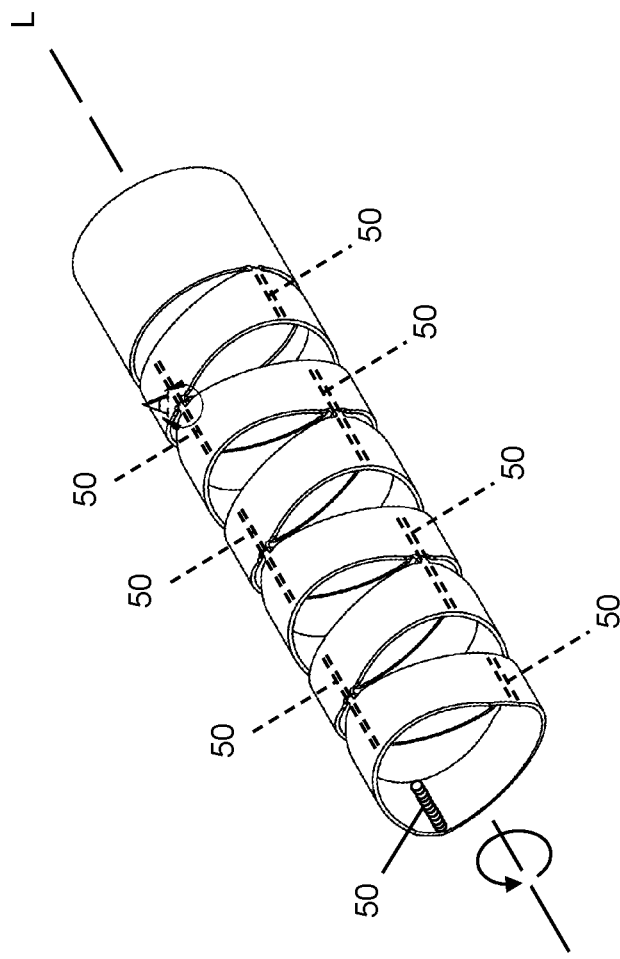
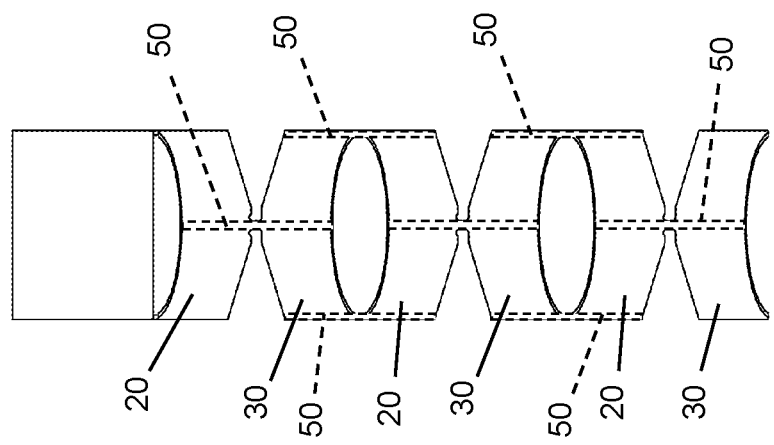

ARTICULATION JOINT MANUFACTURING PROCESS AND WORKPIECE THEREFOR

CROSS-REFERENCE TO RELATED APPLICATION

This application claims the priority of U.S. Provisional Patent Application No. 62/586,344 filed on Nov. 15, 2017, the entirety of which application is incorporated herein by reference.

BACKGROUND

This disclosure relates generally to articulation joints and the manufacturing process for making such joints. More particularly, this disclosure relates to manufacturing techniques for elongated articulation joints such as may, for example, be employed in endoscope probes.

SUMMARY

Briefly stated, a method for manufacturing an articulation joint in one preferred embodiment comprises cutting an elongated tube to form a multiplicity of links wherein adjacent links are connected by a bridge. The method further comprises forming a fracturable portion on each bridge and connecting a multiplicity of springs to adjacent links to form a workpiece having a longitudinal axis. The method further comprises applying a torsional force to the workpiece to fracture each of the bridges to thereby form an articulation joint comprising a series of links wherein adjacent links are connected by at least one spring.

The step of cutting an elongated tube preferably employs a laser. The step of forming a fracturable portion on each bridge also preferably employs a laser. The step of connecting a multiplicity of springs is preferably performed by welding the springs to the links.

The method may further comprise positioning the springs on a mandrel prior to connecting the springs to adjacent links. The method may also comprise cutting the links to form multiple link pairs and a pair of opposed bridges between each adjacent link. The step of forming a fracturable portion is accomplished by forming an indentation, which may be a score, a perforation, an elongated indentation or an oval shaped indentation. Preferably, two diametrically positioned springs connect each adjacent link. One of the workpiece ends is fixed relative to the other end portion and a method step further comprises applying a torsional force to the opposite end portion.

The method for manufacturing articulation joints comprises in another embodiment cutting an elongated tube to form a multiplicity of adjacent links and a pair of opposed bridges between each said adjacent link and forming link pairs wherein adjacent links are connected by a bridge.

The manufacturing method comprises connecting a multiplicity of springs to adjacent links to form a workpiece and applying a torsional force to the workpiece to fracture each bridge to thereby form an articulation joint workpiece stage comprising a series of links wherein adjacent links are connected by at least one spring. The manufacturing method preferably employs a laser to cut the elongated tube and the springs are connected by welding the springs to the links. The springs are preferably positioned on a mandrel prior to connecting the springs to the link. A score, a perforation, an elongated indentation or an oval shaped indentation may form the fracturable portion on at least one of the bridges.

The manufacturing method preferably comprises connecting two diametrically positioned springs to connect each adjacent link.

A workpiece for producing an articulation joint comprises an elongated member configured in a longitudinal series of links having a generally uniform maximum outside diameter and an inside surface. A bridge connects each adjacent pair of links and each bridge has a narrow fracturable portion. A multiplicity of springs are installed wherein each spring is affixed at the inside surface of each adjacent pair of links and connects adjacent links.

Preferably, two diametrically opposed bridges connect each adjacent pair of links. The fracturable portion may be defined by a score, a perforation, an elongated indentation and an oval indentation. A pair of diametrically opposed springs connect each adjacent pair of links wherein each said spring is positioned inside of the elongated member adjacent a bridge. For a link interposed between adjacent links, one pair of bridges connecting one link is oriented 90° opposite a pair of bridges connecting the other link. Each link has opposed edges with angularly oriented alternating convex/concave contours.

BRIEF DESCRIPTION OF THE DRAWINGS

FIG. 2 is a top plan view of the workpiece segment of FIG. 1, the bottom plan view being identical;

FIG. 3 is a perspective view, partly diagrammatic, of a second workpiece segment for an articulation joint for a manufacturing process;

FIG. 3A is an enlarged annotated view of a modified portion B of FIG. 3;

FIG. 4 is a top plan view, partly diagrammatic, of the workpiece segment of FIG. 3, the bottom plan view being identical;

FIG. 5 is a top plan view of a subsequent stage workpiece segment incorporating the workpiece segment of FIG. 1, portions shown in phantom, the bottom plan view being identical;

FIG. 6 is a perspective view, portions shown in phantom, of the subsequent stage workpiece segment of FIG. 5;

DETAILED DESCRIPTION

Figure 9:
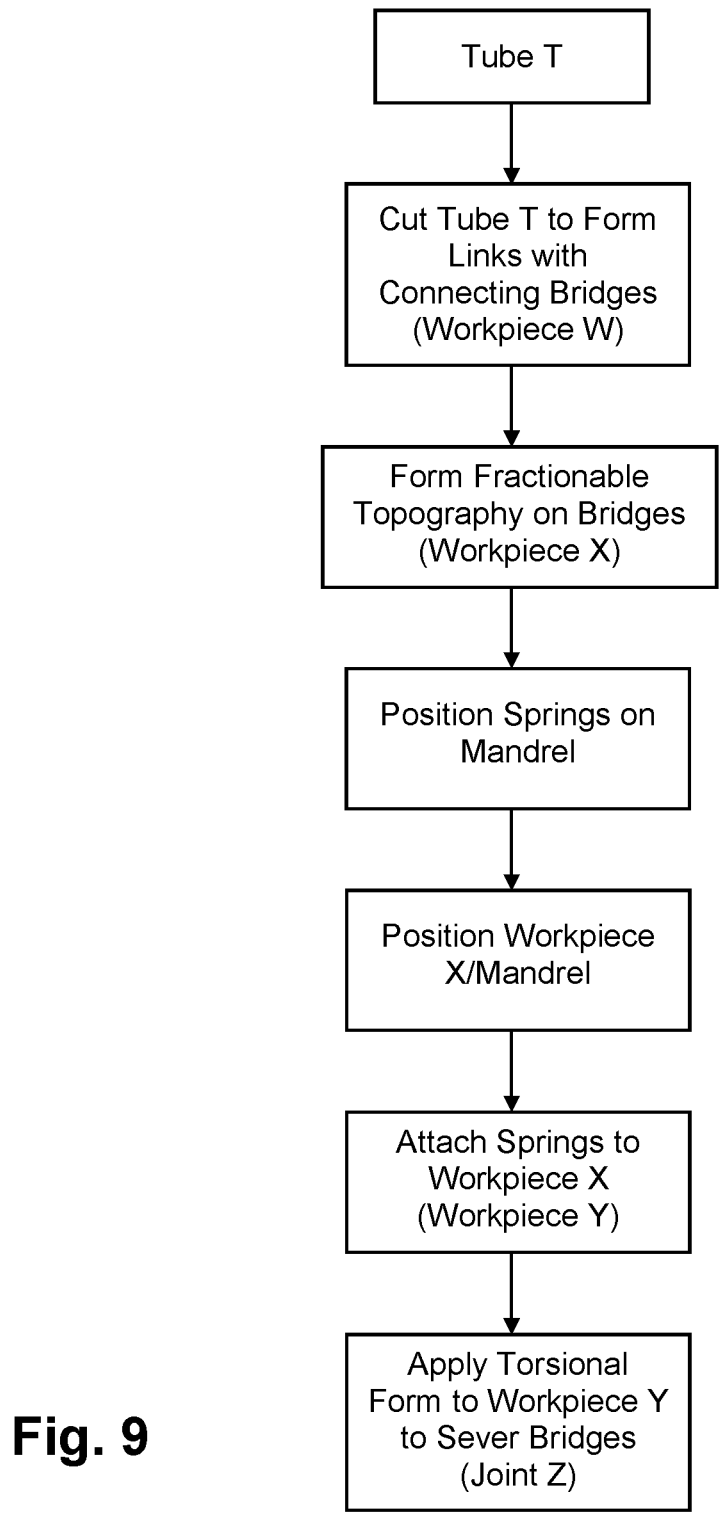
FIG. 9 is a functional block diagram illustrating steps in a manufacturing process for an articulation joint.

With reference to the drawings wherein like numerals represent like parts throughout the figures, the steps of a manufacturing process for producing an articulation joint, such as, for example, may be employed in an endoscope probe, is functionally described in FIG. 9 in general form.

The manufacturing process commences with elongated thin walled stainless steel tubes which may, for example, be 5 feet or any other length and typically have a uniform outside diameter of ⅜ to ½ inches. Other tube dimensions and materials are possible. The steel tube is cut—preferably by means of a laser—to form a longitudinal series of links 20 and 30. The links are essentially cut and formed in pairs 10. Links 20 and 30 preferably are quasi-mirror image structures with opposite relative longitudinal orientations and equal corresponding dimensions. Adjacent links are connected by means of a bridge 40 in an initial workpiece designated W in FIG. 1 and W' in FIG. 3.

Figure 1A:
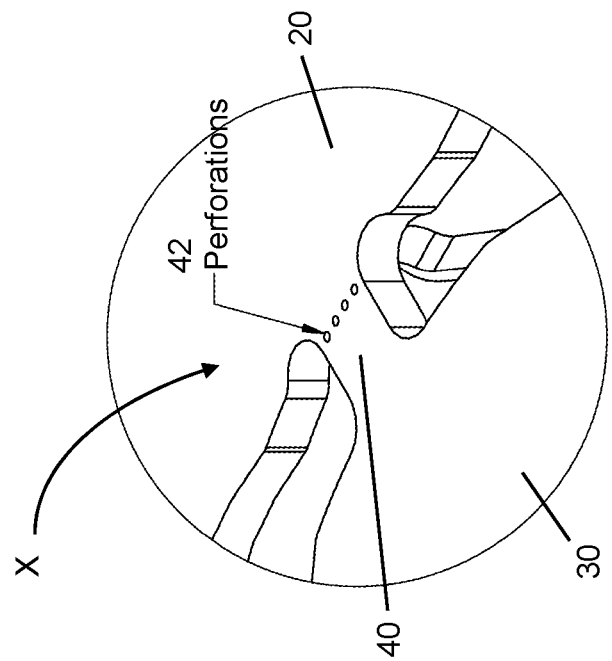
FIG. 1A is an enlarged annotated view of a modified portion A of FIG. 1.
Figure 1:
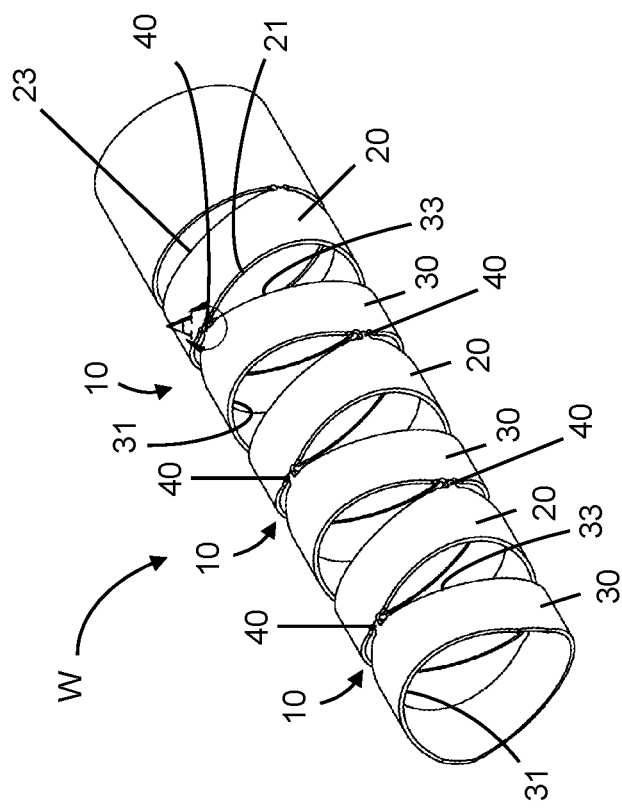
FIG. 1 is a perspective view of a representative portion of an intermediate workpiece for an articulation joint manufacturing process.

It should be appreciated that the segments shown in FIGS. 1 and 3 are representative segments of a significantly longer structure with significantly many more such links.

In preferred form, there are two bridges 40 between each adjacent link 20 and 30. The bridges 40 are preferably disposed at diametrically opposed portions of the link when viewed from the end or cross-sectional view. The links 20 and 30 are preferably formed in axially symmetric fashion about a central longitudinal axis L in an alternating opposed fashion so that dual arcuate concave curves or contours 22 or 32 are formed on one edge 21 or 31 and dual complementary convex curves or contours 24 or 34 are formed at the opposite edge 23 or 33 at a given angular position about axis L.

Figure 1B:
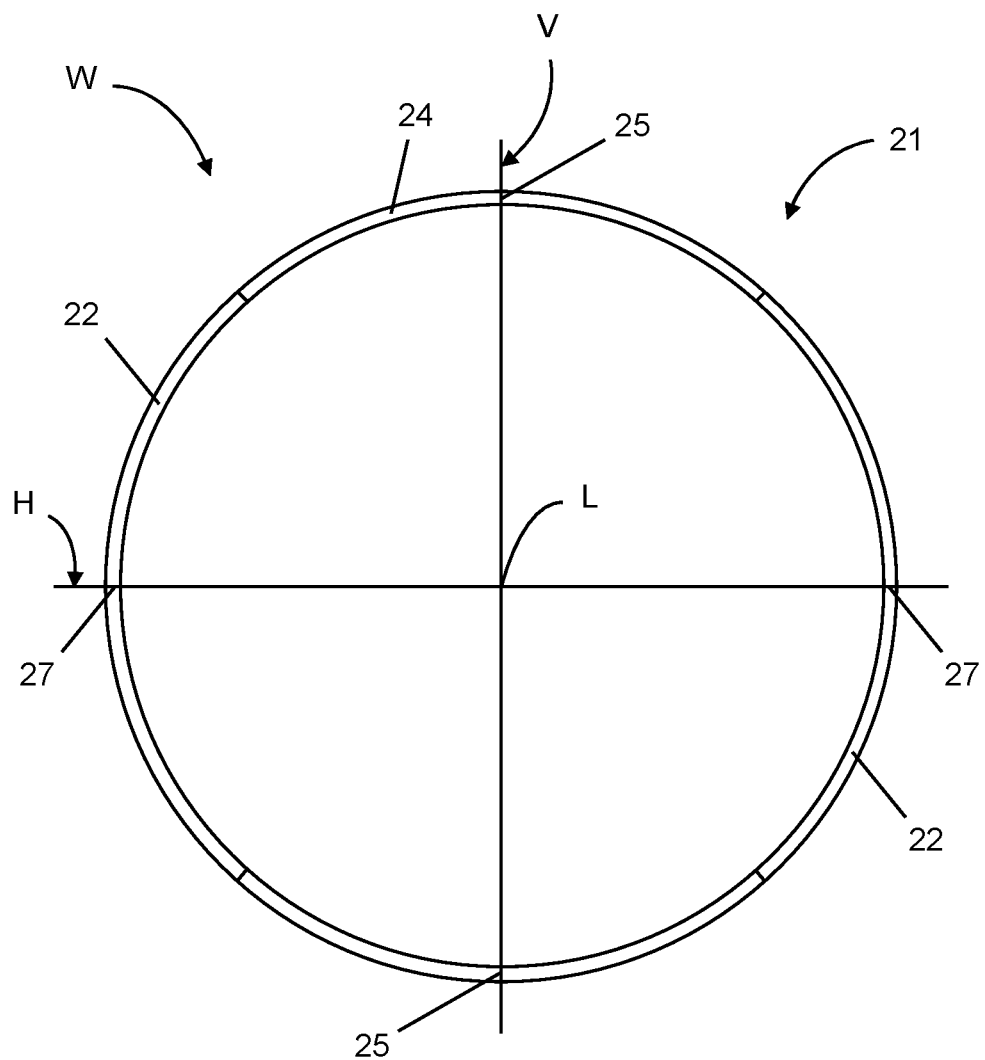
FIGS. 1B, 1C, 1D and 1E are enlarged end views, partly diagrammatic, of one edge of adjacent links of the workpiece portion of FIG. 1.
Figure 1C:
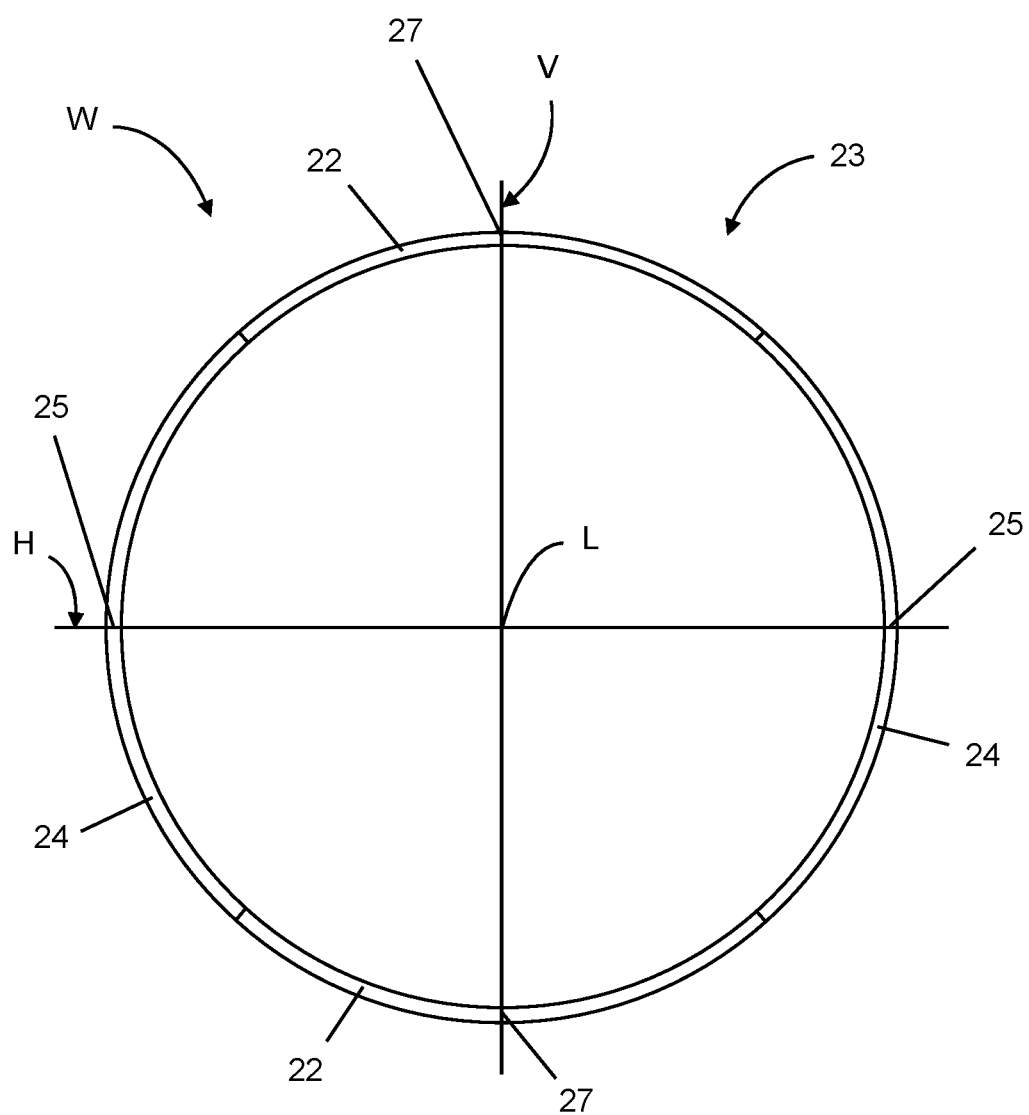

The edges are preferably symmetric relative to a horizontal plane H or a vertical plane V through the central axis L. FIGS. 1B and 1C, which are opposite end views of link 20, are illustrative of edge 21 and edge 23. Edge 21 has diametrically opposite convex portions each with a medial apex 25 and a medial inflexion 27. Edge 23 also has diametrically opposite convex portions with a medial apex 25 and diametrically opposite concave portions with a medial inflexion 27 with the respective apices and inflexions of edge 21 and edge 23 being angularly offset at 90°.

Figure 1D:
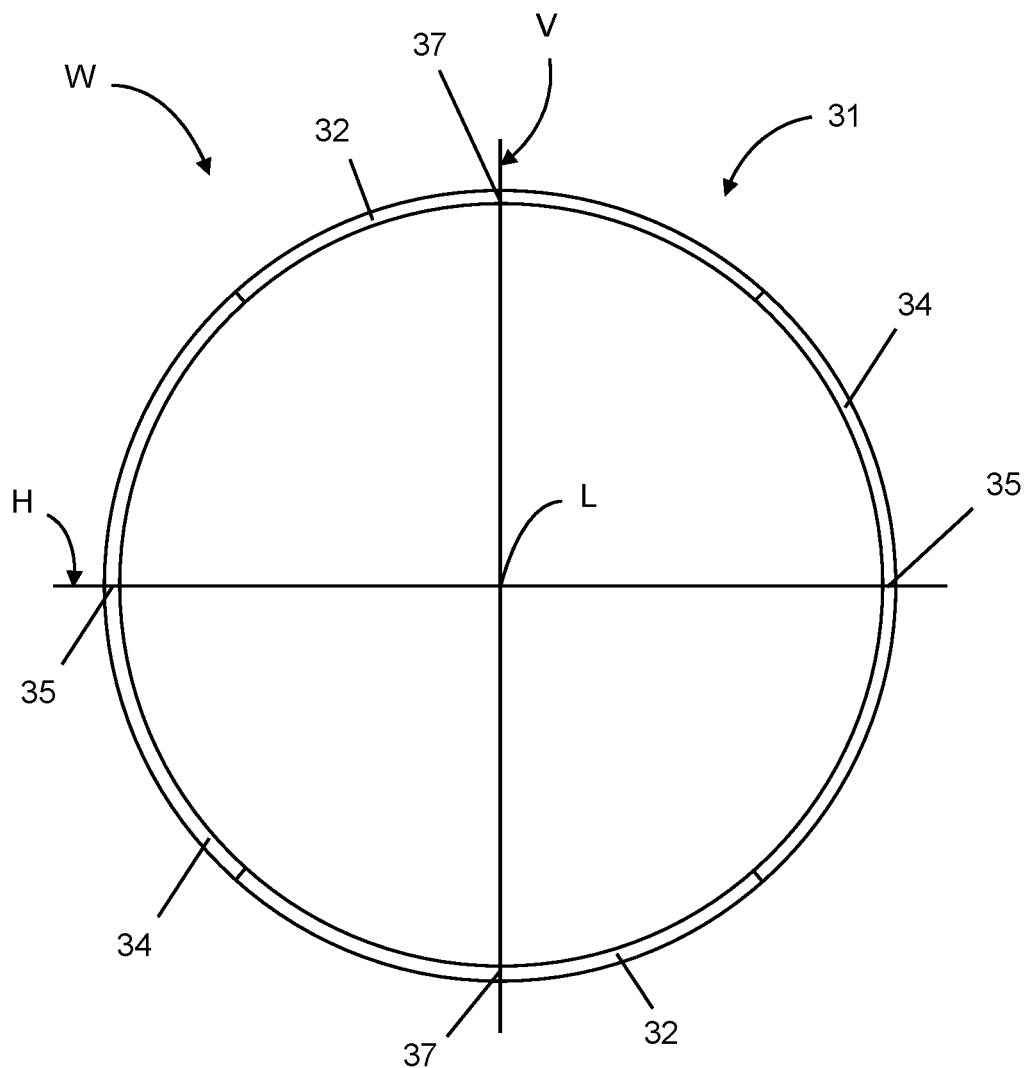
Figure 1E:
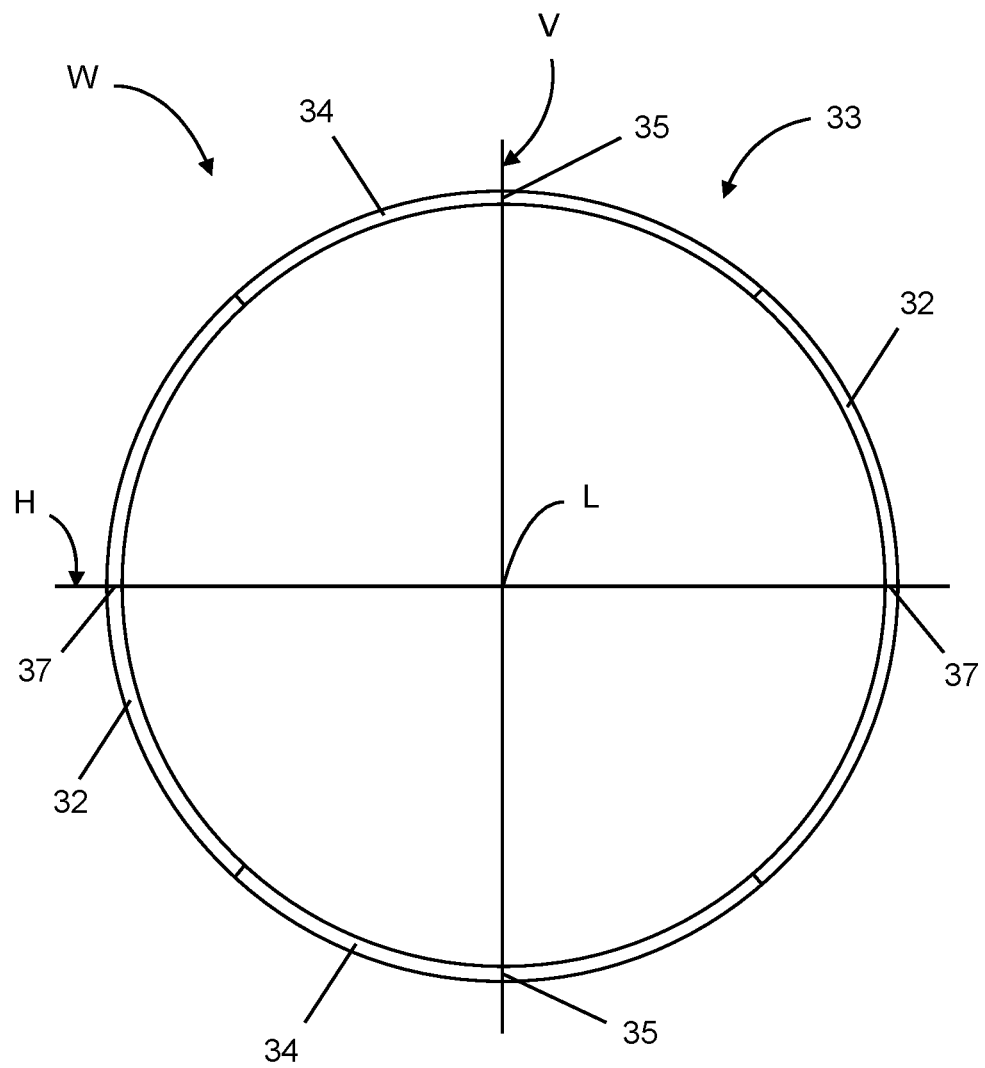
Figure 7:
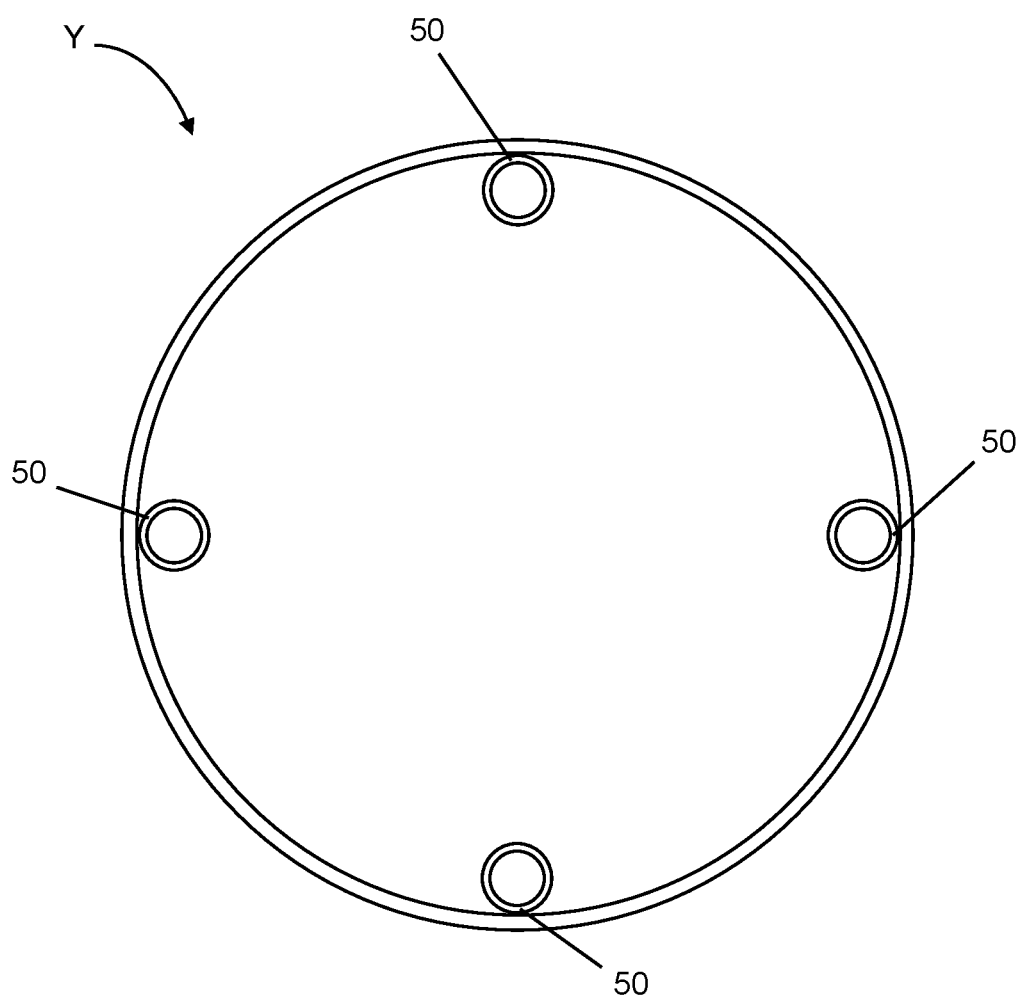
FIG. 7 is a sectional top plan view of the subsequent stage workpiece segment of FIG. 5.

FIGS. 1D and 1E, which are opposite end views of link 30, are illustrative of edge 31 and edge 33. Edge 31 has diametrically opposed convex portions with medial apices 35 and diametrically opposed concave portions with diametrically opposed medial inflexions 37. Likewise, edge 33 has diametrically opposed convex portions diametrically opposed with medial apices 35 and diametrically opposed concave portions with diametrically opposed medial inflexions 37 which are offset 90° with respect to those of edge 31. The concave portions 24 and 34 may be slightly irregular in the vicinity of the apices 25 and 35. Alternative link configurations and geometrics are possible.

In the workpiece of FIG. 1, bridges 40 extend between the adjacent convex apices 25 and 35. Adjacent apices oppose each other in quasi convergent fashion. Consequently, when viewed from the top and the bottom, there will be corresponding link pairs with bridges 40 connecting to adjacent links and from the diametrically opposite position, there will also be two adjacent convergent apexes with bridges connecting those links.

Torsion springs 50, which have a length preferably substantially commensurate with the extreme distance D between apices of a link pair (FIG. 4), are positioned on a mandrel. The mandrel is alignable inside the workpiece. The medial portions of the springs 50 are longitudinally and angularly alignable at substantially the interior portion below the bridges 40. The opposed end spring segments are then welded to the adjacent link at the underside connecting pairs of the tubes to produce workpiece Y. Consequently, it will be appreciated that each link 20, 30 has two pairs of bridges 40 and two corresponding pairs of torsion springs 50 extending to connect with the next adjacent link of each link.

It will be appreciated that the bridges 40 provide a narrow connecting structure in the initial workpiece W. Each of the bridges 40 has a narrow breakaway portion or fracturable topography in workpiece Y preferably produced by an indentation which may be in the form of perforations 42 (FIG. 1A), a score 44 (FIG. 3A), an elongated slot, an oval shaped indentation or other type of indentation. The indentations are preferably formed by a laser. Other forms of the fracturable topography and forming techniques may also be employed.

The bridge indentation fracturable topography feature (designated as workpiece X upon completion) functions so that the bridge will sever or fracture under a pre-established torsion force applied to the workpiece about axis L. The springs 50, however, will remain connected to the links 20, 30 as previously described.

Figure 8A:
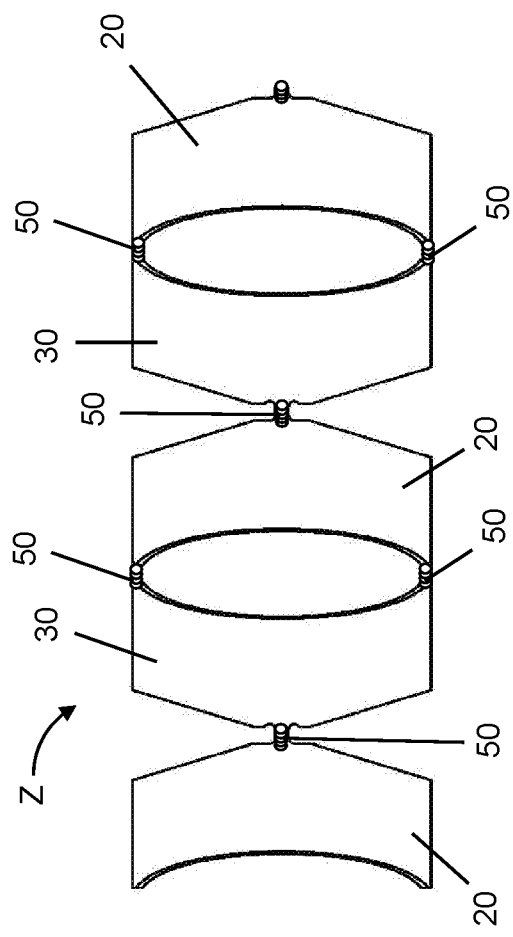
FIG. 8A is a top plan view of an articulation portion of a joint, the bottom plan view being identical.
Figure 8B:
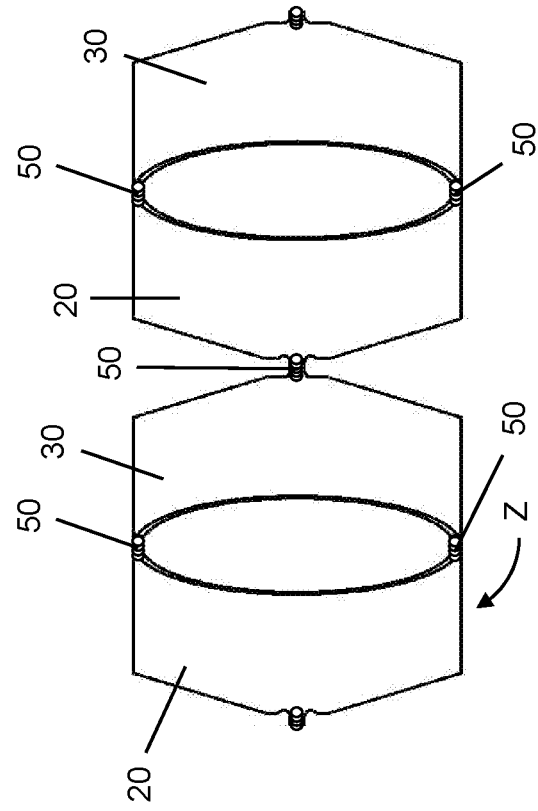
FIG. 8B is a side view of the joint portion of FIG. 8A, the opposite view being identical.

After the springs have been welded in place, the workpiece Y is subjected to a torsion-like twisting force between each end about the central longitudinal axis L (See FIG. 6). The force is sufficient to sever or fracture the bridges, such as illustrated in FIGS. 8A and 8B to form articulation joint Z. It will be appreciated that upon severing or fracturing the bridges 40, the links 20 and 30 are still connected by the torsion springs 50.

FIG. 9 illustrates the manufacturing process from tube T to workpiece W to workpiece X to workpiece Y to articulation joint Z.

In the preferred application, a sheath encloses the articulation joint and various interior components are ultimately received such as fiber optic cables. Conductive strands are received at the interior of the sheath. The severed workpiece thus provides a very sturdy, multiple directional, versatile and reliable articulation joint along a significant distance for a probe.

While preferred embodiments of the manufacturing process and workpiece have been set forth for purposes of illustration, the foregoing description should not be deemed a limitation of the invention herein. Accordingly, various modifications, adaptations and alternatives may occur to one skilled in the art without departing from the spirit and the scope of the present invention.

The invention claimed is:

1. A method for manufacturing an articulation joint comprising:
   (a) cutting an elongated tube to form a multiplicity of links wherein adjacent links are connected by a bridge;
   (b) forming a fracturable portion on each bridge;
   (c) connecting a multiplicity of springs to adjacent links to form a workpiece having a longitudinal axis;
   (d) applying a torsional force to said workpiece about said axis to fracture each said bridge to form an articulation joint comprising a series of links wherein adjacent links are connected by at least one spring.

2. The method of claim 1 wherein step (a) employs a laser.

3. The method of claim 1 wherein step (b) employs a laser.

4. The method of claim 1 wherein step (c) is performed by a welding the springs to the links.

5. The method of claim 1 further comprising positioning said springs on a mandrel prior to step (c).

6. The method of claim 1 wherein step (a) further comprises cutting said links to form multiple link pairs and a pair of opposed bridges between each said adjacent link.

7. The method of claim 1 wherein said fracturable portion is produced by forming an indentation selected from the group consisting of a score, a perforation, an elongated indentation and an oval shaped indentation.

8. The method of claim 1 wherein step (c) further comprises connecting two diametrically positioned springs to connect each adjacent link.

9. The method of claim 1 wherein step (d) further comprises fixing one end portion of said workpiece and applying a torsional force to the opposite end portion.

10. A method for manufacturing an articulation joint comprising:
(a) cutting an elongated tube to form a multiplicity of adjacent links and a pair of opposed bridges between each said adjacent link and forming link pairs wherein adjacent links are connected by a bridge;
(b) connecting a multiplicity of springs to adjacent links to form a workpiece;
(c) applying a torsional force to said workpiece to fracture each said bridge to form an articulation joint comprising a series of links wherein adjacent links are connected by at least one spring.

11. The method of claim 10 wherein step (a) is performed by a laser.

12. The method of claim 10 wherein step (b) is performed by a welding the springs to the links.

13. The method of claim 12 further comprising positioning said springs on a mandrel prior to step (b).

14. The method of claim 10 further comprising forming a fracturable portion on at least one said bridge produced by forming an indentation selected from the group consisting of a score, a perforation, an elongated indentation and an oval shaped indentation.

15. The method of claim 10 wherein step (b) further comprises connecting two diametrically positioned springs to connect each adjacent link.

16. A workpiece for producing an articulation joint comprising:
an elongated member configured in a longitudinal series of links having a generally uniform maximum outside diameter and an inside surface;
a bridge connecting each adjacent pair of links, each said bridge defining a fracturable portion; and
a multiplicity of springs, each spring connected at the inside surface of each adjacent pair of links.

17. The workpiece of claim 16 further comprising two diametrically opposed bridges connecting each adjacent pair of links.

18. The workpiece of claim 16 wherein said fracturable portion is defined by an indentation selected from the group comprising a score, a perforation, an elongated indentation and an oval indentation.

19. The workpiece of claim 16 further comprising a pair of diametrically opposite springs connected to each said adjacent pair of links.

20. The workpiece of claim 19 wherein each said spring is positioned at the inside of said elongated member adjacent a said bridge.

* * * * *